United States Patent
Jessup

(10) Patent No.: US 6,280,741 B1
(45) Date of Patent: Aug. 28, 2001

(54) EQUINE TREATMENT AND METHOD OF ADMINISTERING SUCH TREATMENT

(76) Inventor: Ed C. Jessup, #15 Country Club Dr., Canyon, TX (US) 79105

(*) Notice: Subject to any disclaimer, the term of this patent is extended or adjusted under 35 U.S.C. 154(b) by 0 days.

(21) Appl. No.: 09/377,088

(22) Filed: Aug. 19, 1999

(51) Int. Cl.[7] .................................................. A61K 39/102
(52) U.S. Cl. ..................................... 424/256.1; 424/234.1; 424/93.1; 435/243
(58) Field of Search ............................... 424/93.1, 234.1, 424/256.1, 203.1; 435/101, 243

(56) References Cited

U.S. PATENT DOCUMENTS

| | | |
|---|---|---|
| 4,701,323 | 10/1987 | Roth et al. . |
| 4,877,613 | 10/1989 | Vedros et al. . |
| 4,981,685 | 1/1991 | Healy . |
| 5,456,914 | 10/1995 | Stine et al. ........................ 424/256.1 |

OTHER PUBLICATIONS

1995, *Haemophilus and Taylorella*, in Essentials of Veterinary Medicine 189–93 (5th ed. G.R. Carter, M.M. Chengappa, A.W. Roberts, eds.).

S. Rosendal and D.A. Boyd, *Hemophilus*, in Pathogenesis Of Bacterial Infections In Animals 132–36 (C.L. Gyles and C.O. Thoen eds.)

1982, Equine Medicine And Surgery, 1045–8 (R.A. Mansmann, E.S. McAllister, P.W. Pratt eds.).

1993–4 Vetrinary Pharmaceuticals And Biologicals 445–7, 506, 675–6, 711 (8th ed. L. Darling ed.).

1985, Pathology Of Domestic Animals, 63–4 (K.V.F. Jubb, P.C. Kennedy, N. Palmer eds.).

*Pathogenesis of Bacterial Infections in Animals*, 132–136, (S. Rosendal and D. A. Boyd).

*Considerations on the Pathogenesis of Navicular Disease*, in Equine Veterinary Science 4–8 (K.N. Thompson, PhD., J.R. Rooney, DVM; M.B. Petrictes–Murphy, DVM, PhD.).

*Treatmen and pathogenesis of navicular disease ('syndrome') in horses*, in Equine Veterinary Journal 478–481.

*Pathophysiology of Navicular Syndrome*, in Veterinary Clinics of North America: Equine Practice 108–129 (vol. 5, No. 1, Apr. 1989, Roy R. Pool, DVM, PhD., Dennis M. Meagher, DVM, PhD, and Susan M. Stover, DVM, PhD).

*Navicular Disease in the Horse*, in Journal of Equine Veterinary Science 19–24 (vol. 16, No. 1, 1996, R.J. Rose DVSc, FRCVS, DipVetAn, MACVSc).

*Biochemical considerations in the treatment of navicular disease*, in TEH Veterinary Record 109*114 (1993, I.,M. Wright J. Douglas).

*Diagonsis and Treatment of the Navicular Syndrome in Horses*, in Veterinary Clinics Of North America: Equine Practice 131–145 (vol. 5, No. 1, Apr. 1989, Tracey A. Turner, DVM, MS).

*The Navicular Syndrom*, in Journal of Equine Veterinary Science 408–410 (vol. 14, No. 8, 1994, Richard L. Asquith, DVM adn Jan Kivipelto MS).

*Navicular Disease vs. Navicular Syndrom*, in Equine Practice 20–22 (vol. 16, No. 3, Mar. 1994, Patrick Colahan, DVM).

*Navicular Disease in the Horse: The Effect of Controlled Intrabursal Corticoid Injection*, in Equine Veterinary Science 316–320 (Jul./Aug. 1990, F. Verschooten, DVM, P. Desmet, DVM, K. Peremans, DVM and T. Picavet, DVM).

*The Blood Supply of Normal and Diseased Navicular Bones*, in Veterinary Radiology 276–281 (vol. 29, No. 6,1 1988, B. Hertsch, H. Dammer).

*The Nature of Enlarged "Vascular Channels" in the Navicular Bone of the Horse*, in the Veterinary Radiology 60–64 (vol. 29, No. 2, 1988, Paul W. Poulus, DVM, PhD, Michael F. Smith, DVM).

*The Improtance of the Lateroedical View for the Radiographic Diagnosis of Navicular Disease*, in Horses 1 Lateromedal View And Navicular Disease 172–180 (F. Verschooten).

*An Effective Shoe for Navicular Disease*, in Journal Of Equine Veterinary Science 295–298 (vol. 14, No. 6, 1994, Robert M. Miller, DVM).

*Treating Navicular Disease*, in Veterinary Medicine 454–459 (May 1997, Mark V. Crisman, DVM, MS, Dipl. ACVIM, R. Scott Pleasant, DVM, MS, Dipl. ACVS).

*Therapy for Navicular Disease*, in The Compendium 1462–1466 (North American Edition, Gayle W. Trotter, DVM, MS Diplomate, ACVS).

*Primary Examiner*—Jennifer E. Graser
(74) *Attorney, Agent, or Firm*—Bracewell & Patterson LLP

(57) ABSTRACT

The invention is directed to a novel method for the use of vaccines to be used in the treatment and/or prevention of Navicular Disease in horses. The method comprises administration of a preparation of *Haemophilus somnus* (*H. somnus*) and/or *Haemophilus ovis* (*H. ovis*) or a combination of *H. somnus* and *H. ovis* antigen, by intramuscular injection. Vaccination with antigens specific to these bacilli will prevent onset of Navicular Disease and will prevent further degeneration of the Navicular bone and bursa in animals afflicted with the disease.

6 Claims, No Drawings

EQUINE TREATMENT AND METHOD OF ADMINISTERING SUCH TREATMENT

BACKGROUND OF THE INVENTION

Navicular disease, also referred to as Podotrochlosis or Podotrochlitis, is essentially a chronic degenerative condition of the Navicluar bursa and the Navicular bone. This condition involves damage to the flexor surface of the bone and to the overlying deep digital flexor tendon, with osteophyte formation on the lateral and proximal borders of the bone. The syndrome has a complex pathogenesis with a heretofore unknown disease origin. It afflicts primarily the forefeet of horses and is essentially unknown in ponies or donkeys. Either *Haemophilus somnus* (*H. somnus*) or *Histophilus ovis* (*H. ovis*) or both is/are the putative cause(s) of Navicular disease in horses. Both organisms are gram negative, non-motile, non-spore forming, pleomorphic coccobacilli. *H. ovis,* an organism commonly found in sheep, is closely related to *H. somnus. Haemophilus agni* (*H. agni*) is another member of the Haemophilus genus that is virtually indistinguishable from *H. somnus*. Therefore, these antigens specific to *H. agni* may also prove beneficial in the treatment and/or prevention of Navicular disease.

*H. somnus* causes infectious thromboembolic meningitis (TEME) in cattle. Preparations of *H. somnus* bacterin have been used prophylactically to prevent TEME. *H. somnus* circulates in the bloodstream of the infected animal and can cause severe vasculitis, hemorrhage, thrombosis and/or infarction in many of the afflicted animal's organs. Thrombosis is an intravascular blood clot found at the point of its origin. All or part of a thrombosis may break off the vessel and be carried through the blood stream as an embolus. The embolus may lodge distally at a narrow point in the animal's vasculature further resulting in either an aneurysm or edema.

Examination of horses afflicted with Navicular disease reveals degenerative lesions in the Navicular bone and changes in the shape of the vascular channels supplying nutrients to the bursa and Navicular bone. This disease pathology may occur due to embolism blockage of the Navicular bone's vasculature, which creates edema in the bursa. Bursa edema places pressure on the surrounding nerves, inducing pain in the horse's hoof, which may further result in lameness in the afflicted animal.

Navicular disease initially manifests itself as intermittent lameness, shortened strides, and a possible tendency to stumble. An afflicted horse relieves the pressure of the deep flexor tendon on the painful area by pointing or advancing the affected foot, with the heel off the ground, resulting in the animal's altered gait. Radiographs of the hoof will further reveal degenerative lesions in the Navicular bone, with a change in shape of the vascular channels from their normal hair-line appearance to a triangular or inverted flask shape. Such lesions may result from either aging or onset of disease and must be interpreted in light of the animal's history and other clinical findings.

Navicular disease is both chronic and degenerative. Use of this novel process will prevent further Navicular disease related degeneration of the bursa. Hoof degeneration as a result of Navicular disease often times leads to euthanizing the animal. Until this novel therapy, Navicular disease was incurable with only palliative measures available for treatment of the afflicted animal. This treatment should vastly prolong the life and usefulness of horses afflicted with this disease.

The treatment of the present disclosure is a preventative for the development of this disease. In a horse which is otherwise unmarked by this disease, administration of this treatment serves as a preventative, i.e., vaccination. It provides what is thought to be fairly long protection. By that, the protection from a single vaccination is some number of months, but it is conjectured that the protection can be extended with periodic renewals. It may be that sufficient protection is achieved in a healthy adult horse after three to six spaced vaccination dosages that lifetime immunity is achieved. However, the outside limit of that duration is not yet fully known in the absence of conducting life time tests which would implicate many years of testing and observation.

In another aspect of the present disclosure, the Navicular disease is arrested by administration of the vaccination procedure set forth in this disclosure. Assume that an adult horse has the onset of a Navicular disease. As soon as some lameness is noted, and upon examination including radiographs as appropriate, the vaccination procedure is then started. A series of treatments is administered as will be described. Ultimately, the horse is treated some number of times sufficient to arrest the Navicular disease. Assume for purposes of discussion that the onset of the disease damaged the flexor surface of the bone. Assume that this amounts to about 20% of that surface. As a generalization, this treatment will stop the further degeneration of the joint. The further progression of the Navicular disease and the resultant degeneration is arrested. If it is caught in time, the animal can be restored to usefulness and can be brought to a state where the animal is substantially free of the disease. Accordingly, disease progress is limited. While it is not shown yet that regeneration occurs, further degradation is stopped. It is believed that this will substantially extend the useful life of diseased horses so that, even though injured, they still have some relative mobility. Lameness as a result of the affliction is capped.

Navicular disease is distinguishable from other diseases affecting the bursa and Navicular bone, such as ringbone (by definition, located at another joint). The treatment disclosed in these claims will not prevent onset or progression of other degenerative joint diseases including chronic osteoarthritis, ringbone, or spavin, which have different physiological origins. Faulty conformation, repeated trauma to the Navicular bone and bursa, and undue stress are the rather common factors contributing to joint degeneration in horses (e.g., ringbone).

The treatment in accordance with present disclosure uses a standard level of potency of a medication which is sometimes known as Somnugen (a trademark of BIOCEUTIC). Potency of the treatment will be discussed below. In general terms, the product known as Somnugen and Bar Somnus are prepared from highly immunogenic strains of *Haemophilus somnus*. The potent vaccine is administered in the fashion set forth below.

The injections are administered deep (1 ½ 20 g. needle) intramuscular in the neck of the horse. The injections must be low in the ventral region as drainage may be necessary due to abscess formation. Different injection sites in the neck (both sides) are mandatory because of the soreness and swelling which may or may not occur. The stage of the disease seems to have an effect upon the occurrences of swelling and/or soreness. Usually the injection site becomes sore and swollen as do the front feet. The soreness/swelling lasts (depending upon the disease stage) for approximately three to four days. The formation of an abscess at the injection site is repressed by adherence to stringent aseptic techniques. Specific intramuscular injections are definitely necessary. Needle cannulae are to be massaged to prevent vaccine from coming back up to the subdermal area post vaccination.

After one treatment, and to especially aggressively deal with an adult horse which is known to have the Navicular disease, the treatment regimen is repeated. After the first injection, the horse will have sore front feet and a very sore and warmer than usual injection site within 24 to 48 hours post first injection. If not, then the presence of Navicular disease should be questioned. Remember that the soreness may or may not occur when the vaccine is being used as a prophylactic measure and may or may not occur after the 6-month booster vaccination. After an interval, a second injection is given, again ideally in the neck but a different injection site following the same procedure as applied to the first injection. A course of treatment for an adult horse involves six treatments. They are spread over a span of six weeks in the preferred sequence to a longer interval of perhaps 50% longer. When six treatments are administered in six weeks, that basically involves one week spacing between treatments.

After stopping the onset of the active disease, it is sound wisdom to continue with maintenance or booster shots thereafter periodically, for instance one per year. Again, this would require data over the lifetime of many adult horses for which data have not been accumulated.

DETAILED DESCRIPTION OF THE INVENTION

This is a method for preparing a vaccination for treatment and/or prevention of Navicular Disease in horses. The preferred method uses commercially available bacterin preparations of *H. somnus,* such as Somnugen™ (manufactured by BIOCEUTIC) and Bar Somnus™ (formerly a Phillips-Roxane, Anchor product). Other similar, commercial preparations include Somnumune™ (Lextron), Somnu Shield XT™ (Grand Labs), Somnu Shield™ (Grand Labs), and Somnutech™ (BioCor). Other antigens specific for *H. somnus* and/or *H. ovis* and/or *H. agni* may also be used to treat or prevent Navicular Disease. All of the *H. somnus* products have been historically used to treat cattle but not horses.

The preferred method of Navicular disease treatment involves six 5.0 mL injections spaced at one week intervals. These injections should then be followed with a 5.0 mL booster injection six months later. Subsequent injections are to be administered annually using the same dosage of *H. Somnus* preparation and protocol.

Injections are administered intramuscularly (IM) deep into the neck of the horse, commonly using a 1.5 inch 20 gauge needle. Injections must be placed in heavy muscle tissue in the middle third of the horse's neck, as drainage may be required as a result of abscess formation. Needle cannulae are to be massaged to prevent the Navicular disease vaccine from migrating to the subdermal area, post vaccination.

Different injection sites on the horse's neck should be used since soreness and swelling may develop at the injection site. The degree of swelling or soreness expected correlates to the degree of Navicular disease progression in the afflicted animal. Such swelling may last upwards of three to four days. If no swelling or soreness develops at the site of injection and/or the front hooves are not warmer than normal, the presence of Navicular disease should be questioned. Soreness and/or swelling may or may not occur after subsequent injections or in animals being vaccinated for Navicular disease.

Booster shots six months after the initial set of injections is a recommended prophylactic measure. Thereafter, vaccinations should occur annually. Protective vaccination can start when the horse is one year of age. Treatment of pregnant horses can occur three months into pregnancy with no harm to either mare or foal.

The present disclosure is directed to treatment after diagnosis of Navicular disease as evidenced by clinical symptoms. This typically involves investigation and recognition of clinical symptoms such as bilateral or unilateral fore limb lameness. It is suggested the lameness can be improved most of the time. Improvement is typically measured by radiographic or x-ray investigation of lesions in the Navicular bone in the hoof. Treatment often must be accompanied by correction of broken hoof orientation should that be established as one of the symptoms. This depends in part on the extent or measure of lameness. Commonly, lameness was evaluated on some arbitrary scale with grading, and further investigation assisted the evaluation of lameness, i.e., radiology supplementation. For this purpose, the following animals were tested.

Test 1

An older gelded quarter horse was tested. The animal was diagnosed with Navicular disease and apparently had an active case at the time of testing. The clinical response seemed to be moderate, and verification by radiographic investigation showed a marked reduction in the diameter of the "vascular" channels after treatment. The investigation was conducted one year after treatment.

Test 2

This was a six year old quarter horse mare afflicted with the disease. Taking into account six treatments, moderate response was seen beginning at the third week. The treatments were continued for all six sessions spaced at one week intervals. Two weeks after treatment, the clinical response or improvement was evaluated simply as mild or acceptable. Radiographs were taken every two weeks. After two weeks, no radiographic changes were noted, but after four weeks, there was some apparent bone remodeling in the vascular channels. After six weeks, the remodeling was more apparent, while there was no evidence of calcification and configuration. After eight weeks (meaning two weeks after the conclusion of treatment), the resolution of the remodeling changes showed no apparent reduction in the vascular channel diameter. It was concluded by radiographic investigations that there was some type of associated inflammation, or perhaps an osteoclastic-osteoblastic nature. This animal suggested that the therapy duration be extended.

Test 3

This was nine year old quarter horse gelding which showed some minimal radiographic response. Further data was not available because of difficulty of observation.

Test 4

A moderate clinical response was obtained for this twelve year old quarter horse gelding. Of the evaluated horses reported in this disclosure, this showed the most significant changes in the structure of the Navicular bones. There were three or four large cystic lucent areas that were observed radiographically. Beginning at about the second week, remodeling began to show and that was more after four weeks and six weeks of treatment. Significant recovery was obtained for this animal.

Test 5

A good clinical response was obtained for a middle-aged quarter horse gelding. The radiographic response showed an increased bone density and also suggested remodeling of the lesions otherwise visible from a front view of both front feet.

Test 6

This horse was a middle-aged quarter horse gelding. The clinical response was quite good and the radiographic response showed new bone growth filling the central opacities of the Navicular bones of both front feet. This was vouched for by radiographs taken about two months after the conclusion of the six week vaccination routine.

From the foregoing, it is reasonably concluded that specific or nonspecific flexor or surface response on the Navicular bone occurred in more than half the animals. Cautiously, it is thought that was about 75%. The mode of the bone tissue regeneration in the vascular channels was not established. By lengthening the duration of treatment, there may be further slight improvement in individual horses. The potential for prevention of the Navicular disease by the method set forth herein is thought to be promising.

All examples of the preferred embodiment use the injection schedule described herein:

EXAMPLE 1

A vaccine for immunization of animals, especially horses, for treatment or prevention of Navicular disease using a vaccine containing surface polysaccharides and/or somatic polysaccharides specific for *H. somnus*.

EXAMPLE 2

A vaccine for immunization of animals, especially horses, for treatment or prevention of Navicular disease using a vaccine containing surface polysaccharides and/or somatic polysaccharides specific for *H. ovis*.

EXAMPLE 3

A vaccine for immunization of animals, especially horses, for treatment or prevention of Navicular disease using a vaccine containing surface polysaccharides and/or somatic polysaccharides specific for *H. agni*.

EXAMPLE 4

A vaccine for immunization of animals, especially horses, for treatment or prevention of Navicular disease using a vaccine containing surface polysaccharides and/or somatic polysaccharides specific for both *H. somnus* and *H. Ovis*.

EXAMPLE 5

A vaccine for immunization of animals, especially horses, for treatment or prevention of Navicular disease using a vaccine containing surface polysaccharides and/or somatic polysaccharides specific for both *H. somnus* and *H. agni*

EXAMPLE 6

A vaccine for immunization of animals, especially horses, for treatment or prevention of Navicular disease using a vaccine containing surface polysaccharides and/or somatic polysaccharides specific for both *H. ovis* and *H. agni*.

EXAMPLE 7

A vaccine for immunization of animals, especially horses, for treatment or prevention of Navicular disease using a vaccine containing surface polysaccharides and/or somatic polysaccharides specific for *H. ovis*, *H. somnus* and *H. agni*.

EXAMPLE 8

A vaccine for immunization of animals, especially horses, for treatment or prevention of Navicular disease using a vaccine containing a *H. somnus* bacterin preparation.

EXAMPLE 9

A vaccine for immunization of animals, especially horses, for treatment or prevention of Navicular disease using a vaccine containing a *H. ovis* bacterin preparation.

EXAMPLE 10

A vaccine for immunization of animals, especially horses, for treatment or prevention of Navicular disease using a vaccine containing a *H. agni* bacterin preparation.

EXAMPLE 11

A vaccine for immunization of animals, especially horses, for treatment or prevention of Navicular disease using a vaccine containing *H. somnus* and *H. ovis* bacterins.

EXAMPLE 12

A vaccine for immunization of animals, especially horses, for treatment or prevention of Navicular disease using a vaccine containing *H. somnus* and *H. agni* bacterins.

EXAMPLE 13

A vaccine for immunization of animals, especially horses, for treatment or prevention of Navicular disease using a vaccine containing *H. ovis* and *H. agni* bacterins.

EXAMPLE 14

A vaccine for immunization of animals, especially horses, for treatment or prevention of Navicular disease using a vaccine containing *H. somnus*, *H. agni* and *H. ovis* bacterins.

The vaccine, after manufacture, is stored at an acceptable cool temperature. All vaccines are stored at 35–45° F. to assure longevity of the vaccine. Accordingly, it must be protected from high and low temperatures both. The shelf life is limited by the date printed on the vaccine. The shelf life, however, is impacted by temperature and sunlight. Accordingly, it is best stored in a dark container or carton to block out the sunlight. On the day of administration, it can be safely removed and administered later that day perferably kept at the 35 to 45° F. temperature. Ambient temperatures are reasonably tolerated provided that the vaccine is administered with reasonable dispatch.

THEORY OF IMMUNIZATION

Animals and horses in particular have the ability to resist almost all types of organisms or toxins that tend to damage the tissues and organs. This immunity is a result of their immune system that forms antibodies and activated lymphocytes that attack and destroy the specific organisms or toxins. This is an acquired immunity. An additional aspect of immunity results from general processes directed at specific disease organisms. This innate immunity includes the following:

1. Phagocytosis of bacteria and other invaders by white blood cells and cells of the tissue macrophage system.
2. Destruction by the acid secretions of the stomach and by the digestive enzymes of organisms swallowed into the stomach.
3. Resistance of the skin to invasion by organism.
4. Presence in the blood of certain chemical compounds that attach to foreign organisms or toxins and destroy them.

There are two types of acquired immunity. In one, the body develops circulating antibodies that attack invading agents (B cell immunity). In the second type, large numbers of activated lymphocytes are formed which are specifically designed to destroy the foreign agent (T cell immunity). These lymphocytes are located most extensively in the lymph nodes, and are found in other areas as well.

Because an acquired immunity does not occur until after first invasion by a foreign agent, the equine body must first obtain some mechanism for recognizing the initial invasion. Foreign agents (toxin or organism) almost always contain one or more specific chemical compounds in their makeup that are different from all other compounds in the body. In general, these are proteins or large polysaccharides, which initiate the acquired immunity. These substances, called antigens, usually, have a high molecular weight to be antigenic (8000 or greater). Furthermore, the process of antigenicity usually depends upon regularly recurring molecular groups, called epitopes, on the surface of the large molecule, which explains why proteins and large polysaccharides are almost always antigenic, since they both have this type of stereochemical characteristic.

When a specific antigen comes into contact with T and B lymphocytes in the lymphoid tissue, certain of the T lymphocytes are activated as "T" cells and certain B lymphocytes are activated to form antibodies. Both of these types then react highly specifically against the particular type of antigen that initiated their development. B lymphocytes have on their cell membrane surface about 100,000 antibody molecules that will react highly specifically with only the one specific type of antigen. T lymphocytes have on their surface "surface receptor proteins" which are similar to antibodies and are also highly specific for the one specified activating antigen.

TREATMENT OF NAVICULAR DISEASE

In treating Navicular Disease in horses, the present vaccine comprises a killed bacterin and an adjuvant. The preferred bacterin used, Haemophilus, is composed of capsular antigens of the Haemophilus bacteria. The adjuvant system is primarily aluminum hydroxide [$Al(OH)_3$]. This part of the vaccine enhances its activity in the animal.

Dose size is generally regulated on a per animal basis. Unlike chemical medication, biological products are not generally administered by animal weight. The Code of Federal Regulations (9 CFR: Animal and Plant Health Inspection Service, USDA; 1-1-99 Edition), makes reference to dosage but not specific in precise volume or quantity. Obviously, the vaccine liquid volume is a few milliliters or cubic centimeters of the killed bacteria in the adjuvant.

Dosage depends on the formulation source and must be sufficient to provide some of the Haemophilus/mL or an effective dose. The proper amount for injecting the vaccine is "one immunizing dose," which measure is contrasted with chemical based pharmaceuticals commonly provided in proportion to body weight. This dose therefore comprises an effective amount.

While the foregoing is directed to the preferred embodiment, the scope thereof is determined by the claims which follow:

What is claimed is:

1. A method of treating a horse for navicular disease comprising:

administering to said horse an effective amount of an *H. somnus* vaccine, said *H. somnus* vaccine containing a killed bacterin of Haemophilus.

2. The method of claim 1 wherein the effective amount of an *H. somnus* vaccine is at least about 5.0 milliliters.

3. The method of claim 2 wherein said vaccine is administered to the horse at least six times.

4. The method of claim 2 wherein said vaccine is administered to the horse once per week.

5. The method of claim 2 wherein said vaccine is administered to the horse at least periodically.

6. The method of claims 3 to 5 wherein the administering step includes injecting said vaccine into the neck of the horse by intramuscular injection.

* * * * *